(12) United States Patent
Brummel et al.

(10) Patent No.: US 7,489,811 B2
(45) Date of Patent: Feb. 10, 2009

(54) METHOD OF VISUALLY INSPECTING TURBINE BLADES AND OPTICAL INSPECTION SYSTEM THEREFOR

(75) Inventors: Hans-Gerd Johann Brummel, Orlando, FL (US); William Alexander Landi, Devon, PA (US); Dennis Lemieux, Casselberry, FL (US); Michael Twerdochlib, Oviedo, FL (US); Stephen Price Masticola, Kingston, NJ (US)

(73) Assignee: Siemens Energy, Inc., Orlando, FL (US)

( * ) Notice: Subject to any disclaimer, the term of this patent is extended or adjusted under 35 U.S.C. 154(b) by 755 days.

(21) Appl. No.: 10/961,632

(22) Filed: Oct. 8, 2004

(65) Prior Publication Data

US 2006/0078193 A1 Apr. 13, 2006

(51) Int. Cl.
*G06K 9/00* (2006.01)
(52) U.S. Cl. ..................................... 382/152
(58) Field of Classification Search ................. 382/112, 382/141–152, 311; 73/116, 117.2, 117.3, 73/116.01, 166.2, 166.3; 348/92, 125; 702/34, 702/35
See application file for complete search history.

(56) References Cited

U.S. PATENT DOCUMENTS

| | | | |
|---|---|---|---|
| 4,380,172 A | | 4/1983 | Imam et al. |
| 4,446,728 A | * | 5/1984 | Ito ............................... 73/116 |
| 4,646,010 A | | 2/1987 | Bystrom et al. |
| 4,685,335 A | | 8/1987 | Sato et al. |
| 4,955,269 A | | 9/1990 | Kendig et al. |
| 5,125,035 A | * | 6/1992 | McCarthy et al. ........... 382/141 |
| 5,275,052 A | * | 1/1994 | Luttrell et al. ................ 73/619 |
| 5,445,027 A | * | 8/1995 | Zorner ....................... 73/593 |
| 5,625,446 A | * | 4/1997 | Bedard ..................... 356/3.08 |
| 5,670,879 A | | 9/1997 | Zombo et al. |
| 6,153,889 A | * | 11/2000 | Jones ..................... 250/559.45 |
| 6,333,812 B1 | * | 12/2001 | Rose et al. .................. 359/367 |
| 6,929,604 B2 | * | 8/2005 | Stone et al. ................. 600/176 |
| 7,140,240 B2 | * | 11/2006 | Gustafson et al. ............. 73/116 |
| 2006/0038988 A1 | * | 2/2006 | Thermos .................. 356/241.1 |
| 2006/0042083 A1 | * | 3/2006 | Baker et al. ................ 29/889.1 |

OTHER PUBLICATIONS

"Image Deconvolution, Soft Imaging System," http://www.photonics.com, Innovative Products Oct. 2002 Edition, 1996-2004 Lauren Publishing.
CTI: Computerized Thermal Imaging, "About Computerized Thermal Imaging, Inc.," http://www.cti-net.com, Last Edited: Jul. 6, 2004.

* cited by examiner

*Primary Examiner*—Daniel G Mariam

(57) ABSTRACT

An optical inspection system is for visually inspecting the blades of a turbine at turning gear operation. The inspection system includes an imager for capturing images of the blades, an optical passage coupled to the imager and structured to provide maximum viewing area of the blades through an inspection port in the turbine and an illuminating assembly adapted to illuminate the blades while the imager captures images thereof. A method wherein the captured blade images are inspected for blade defects, is also disclosed.

20 Claims, 3 Drawing Sheets

METHOD OF VISUALLY INSPECTING TURBINE BLADES AND OPTICAL INSPECTION SYSTEM THEREFOR

BACKGROUND OF THE INVENTION

1. Field of the Invention

The present invention relates generally to inspection of turbine blades and, more particularly, to an optical inspection system for visually inspecting turbine blades during the turning gear operation. The invention also relates to a method of visually inspecting turbine blades at turning gear.

2. Background Information

Gas and steam turbines for electrical power generation are very expensive (i.e., tens of millions of dollars each). For maximum efficiency, they should not be removed from service for inspection or maintenance unless absolutely necessary. However, defects in the blades of large turbines can cause serious damage and possibly injury. It is, therefore, necessary to be able to promptly detect the formation of blade defects.

Reliable and early detection of failures that could be catastrophic to the power generation unit and the ability to bring the unit through the critical period until the next planned outage, are paramount in keeping repair costs low and guaranteeing long term safe operation. Evaluating the condition of the turbine blade thermal barrier coating (TBC), commonly referred to in the art as TBC-monitoring, is the first step of analyzing the status of the turbine blades. In modern, high-performance gas turbines, for example, TBC-monitoring is necessary to ensure the integrity of the blades.

Known conventional methods of inspecting turbine blades such as surface inspection methods (i.e., magnetic particle testing; eddy current testing; dye penetrant techniques) and volumetric methods (i.e., ultrasonic testing) rely on the periodic disassembly of the turbine. Disassembling a turbine to inspect it is an expensive process and takes the turbine out of service for a significant amount of time. Unfortunately, none of the foregoing techniques are suitable for inspection while the turbine is on-line and running under load. More recent turbine inspection techniques employ a variety of apparatus and methodology in an attempt to offer on-line TBC-monitoring for full load operation.

For example, U.S. Pat. No. 4,380,172 entitled, "On-line Rotor Crack Detection," discloses a method of detecting incipient cracks in the rotor of a fluid powered turbine while the turbine is on-line and running under substantially normal load. Vibrations in the rotor are monitored and a signature analysis of normal vibration patterns is performed in order to establish a vibration spectrum for purposes of comparison. The turbine is then perturbed, for example, by changing the temperature of the motive fluid (i.e., changing the temperature of steam in a steam driven turbine), and the signature analysis is again performed to determine changes in the vibration pattern. An increase in the amplitude of the fundamental frequency and the appearance and increase in amplitude of higher harmonics following perturbation indicates the presence of a defect in the rotor.

U.S. Pat. No. 4,685,335, entitled "Method and Apparatus for Monitoring Cracks of a Rotatable Body," discloses the use of acoustic emissions (AE) signals in order to detect turbine blade cracks. Discovery and evaluation of the crack (i.e., depth of the crack) are accomplished by comparing the AE signals with assumed vibrations of the rotatable body. The method permits discovery of cracking in the rotatable body from its inception and also the progress of cracking on an on-line basis.

U.S. Pat. No. 4,955,269, entitled "Turbine Blade Fatigue Monitor" discloses the use of passive proximity probes to inspect turbine blades. Specifically, an on-line vibratory fatigue monitor measures displacement of the blade to generate a displacement signal and calculate accumulated fatigue in the blade based thereon. The method requires constant monitoring of vibratory displacement and changes in the steady state stress.

U.S. Pat. No. 5,670,879, entitled "Nondestructive Inspection Device and Method for Monitoring Defects Inside a Turbine Engine," discloses another method of monitoring a defective condition in a rotating member of a combustion turbine. The method uses a holder assembly to position an ultrasound transducer or eddy current sensor near the rotating member without disassembling the turbine. Signals indicative of the monitored condition are recorded and compared to a signal representation generated from a reference standard having a known defect so that a defective condition can be discovered.

Unfortunately, each of the foregoing inspection methods and apparatus has its own unique set of disadvantages. The interior environment of a turbine is an extremely hostile environment for electrical equipment (e.g., without limitation, cameras; sensors; illuminating equipment). For example, a gas turbine typically operates at an internal temperature of about 1200° C. (2192° F.) near the "row 1" blades, while a steam turbine can have temperatures of up to about 550° C. (1022° F.). The current state of electronics technology is limited to temperatures well below this. Therefore, working on-line with pyrometers and/or infra red (IR) technology or with one of the other aforementioned apparatus, for example, in such environments requires significant effort in terms of cooling. Generally, 200° C. (392° F.) is considered to be the maximum practical temperature for operating electrical equipment. High pressures and reactive chemistry within turbines provide further detriment to inspection and measurement equipment. Accordingly, it will be appreciated that the foregoing apparatus (e.g., without limitation, IR cameras) and procedures required for on-line turbine blade inspection are very cost intensive.

There is a need, therefore, for a reliable and cost-efficient method and apparatus for visually inspecting turbine blades.

Accordingly, there is room for improvement in the art of turbine blade inspection.

SUMMARY OF THE INVENTION

These needs and others are satisfied by the present invention, which is directed to a method and apparatus for visually inspecting the blades of a turbine while the turbine is kept at turning gear operation when initially taken off-line. Turning gear is a slow rotation of the turbine at between about 3 to 5 RPM. The method employs an optical inspection system using any suitable commercially available imaging apparatus such as a computer controlled display (CCD) camera, to monitor the turbine during turning gear operation. The camera is coupled to the turbine for viewing through an inspection port thereof.

As one aspect of the invention, an optical inspection system is for visually inspecting a blade of a turbine. The turbine includes an inspection port. The optical inspection system comprises: an imager adapted to capture images of the blade while the turbine is at a turning gear operation; a viewing device coupled to the imager and structured to permit the imager to view the blade through the inspection port of the turbine; and an illuminating assembly adapted to illuminate the blade while the imager captures images thereof.

The inspection system may include a local monitoring computer wherein the imager is a computer-controlled camera and wherein the local monitoring computer is adapted to control the camera in order to automate the capturing of images of the blade and the inspection of the images for blade defects.

The viewing device may be an optical passage structured to maximize the amount of the blade which can be viewed through the inspection port, the optical passage including a first end, a second end and an intermediate portion therebetween wherein the first end of the optical passage is coupled to the inspection port and the imager is coupled to the second end of the optical passage. The illuminating assembly may include an illuminating device, a lens for concentrating light emitted from the illuminating device, and a deflector for directing the concentrated light onto the blade wherein the illuminating assembly is coupled to the intermediate portion of the optical passage.

As another aspect of the invention, a method of visually inspecting a turbine during a turning gear operation comprises the steps of: providing a turbine, including a plurality of blades and an inspection port for viewing the plurality of blades, the blades being coupled to a rotating shaft; providing an optical inspection system for visually inspecting at least one of the plurality blades through the inspection port, the optical inspection system including an imager, a viewing device coupled to the imager and adapted to capture images of the at least one of the plurality of the blades through the inspection port, and an illuminating assembly adapted to illuminate the at least one of the plurality of blades while the imager captures images thereof; determining when the turbine is in the turning gear operation; monitoring the position of the shaft of the turbine in order to determine when the at least one of the plurality of blades is in proper view for capturing images; illuminating the at least one of the plurality of blade; capturing images of the at least one of the plurality; deconvolving the images; and analyzing the images in order to determine whether or not any of the plurality of blades has a defect.

The optical inspection system may include a local monitoring computer wherein the local monitoring computer automates one or more of the steps of the method of visually inspecting a turbine during a turning gear operation. The step of analyzing the images for blade defects may include fusing previously acquired images of a blade with the most recently acquired image of the same blade, fusing turbine sensor data and turbine monitoring system output, alarming other monitoring systems when a defect is detected, selecting certain captured images for storage in a local storage bank, and sending selected stored images to other monitoring and control systems.

BRIEF DESCRIPTION OF THE DRAWINGS

A full understanding of the invention can be gained from the following description of the preferred embodiments when read in conjunction with the accompanying drawings in which.

DESCRIPTION OF THE PREFERRED EMBODIMENTS

Figure 1:
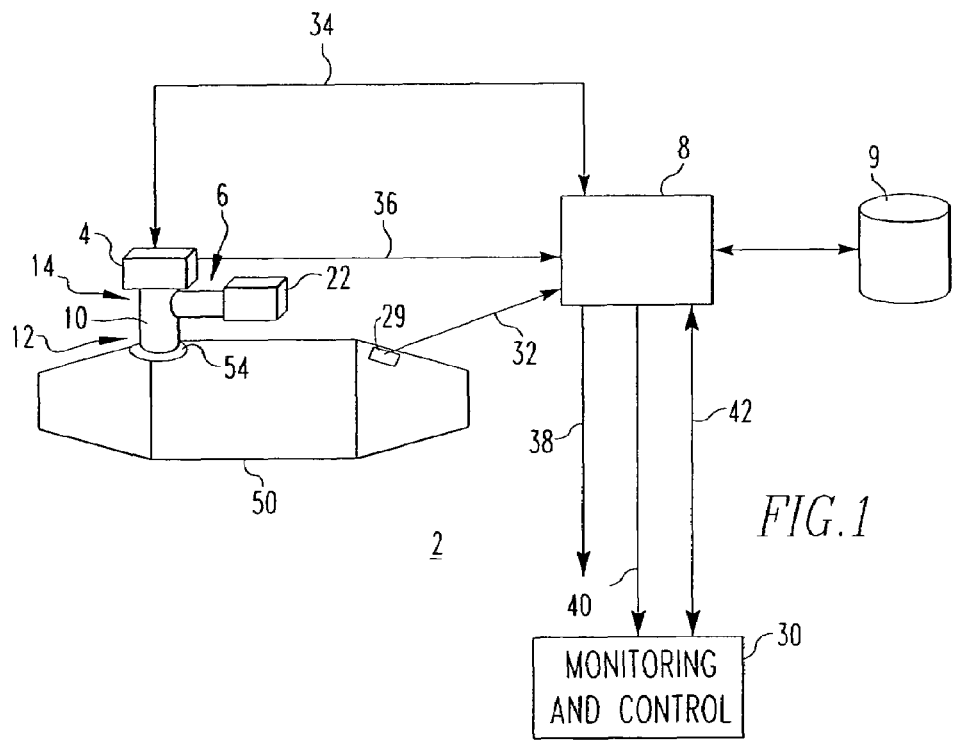
FIG. 1 is a schematic representation of an optical inspection system in accordance with an embodiment of the present invention.

The invention will be described as applied to optical TBC-monitoring of the blades of a power generation station combustion turbine, although it will become apparent that it could also be applied to inspection of the blades of other types of turbines, such as, for example, gas turbines used in aircraft engines and other gas turbines.

For purposes of the description hereinafter, the terms "upper," "lower," "top," "bottom," "left," "right," and derivatives thereof shall relate to the invention, as it is oriented in the drawing figures. However, it is to be understood that the invention may assume various alternatives and step sequences, except where expressly specified to the contrary. It is also to be understood that the specific elements and processes illustrated in the drawings and described in the following specification, are simply exemplary embodiments of the invention. Therefore, specific dimensions, orientations and other physical characteristics related to the embodiments disclosed herein are not to be considered limiting.

As employed herein, the statement that two or more parts are "coupled" together shall mean that the parts are joined together either directly or joined through one or more intermediate parts.

As employed herein, the term "deconvolve" refers to the process of cleaning or improving the clarity of captured blade images, for example, by reducing blur and distortion caused by long-term deterioration of the optics.

As employed herein, the term "sensor" refers to any known or suitable mechanism for collecting data from the exemplary turbine, expressly including but not limited to, thermal sensors (i.e., thermocouples), optical sensors (i.e., photo eyes), pressure sensors (i.e., pressure transducers), position sensors and speed sensors.

FIG. 1 shows a schematic representation of an optical inspection system 2 for visually inspecting the blades 52 (FIG. 2) of a turbine, such as the exemplary combustion turbine 50, shown. The optical inspection system 2 includes an imager, such as the exemplary CCD camera 4, and an illuminating assembly 6 having an illuminating device, such as the exemplary flash 22. The camera 4 and illuminating assembly 6 are used to acquire images of the blades 52 during the turning gear operation of the combustion turbine 50. The illuminating assembly 6, as will be described herein, is adapted to illuminate the blades 52 while the camera 4 captures images thereof. In a preferred embodiment of the invention, the camera 4 is permanently coupled to the turbine 50 at an inspection port 54 (best shown in FIG. 2). The inspection port 54 is positioned such that the camera 4 can monitor the turbine blades 52 as they rotate past the port 54. This procedure of visual inspection at turning gear is much less complicated and thus less expensive than the aforementioned known on-line TBC-monitoring methods at operating temperature and pressure. Additionally, because TBC loss does not instantaneously lead to blade 52 failure but rather develops slowly over a long time period, this method of looking into the turbine 50 during turning gear operation is entirely adequate. Specifically, when taking into account typical operation modes of combustion turbines, start-ups and shutdowns happen frequently, almost daily. Therefore, turbines 50 are in turning gear operation for a sufficient amount of time to assure detection of TBC losses or other damage at a very early stage.

As shown in FIG. 1, the exemplary optical inspection system 2 includes a viewing device 10. The exemplary viewing device is an optical passage 10 including a first end 12, a second end 14 and an intermediate portion therebetween. As will be discussed in greater detail hereinbelow, the exemplary optical passage 10 is structured such that the camera 4 may view substantially all of a blade 52 through the inspection port 54 in order to capture images thereof. The images are then reviewed or analyzed in order to detect blade defects. In the exemplary optical inspection system 2, acquisition of the blade images is automated and controlled by a local monitoring computer 8. The local monitoring computer 8 is in electrical communication with, for example, sensors 29 within the turbine 50 and other monitoring and control systems (indicated generally by reference 30 in FIG. 1). For example, shaft 56 (FIG. 2) rotational speed and position data 32 acquired by sensors 29 at the turbine 50 may be received by the local monitoring computer 8 in order to determine, respectively, when the turbine 50 is on turning gear and when a particular blade 52 is in proper view for capturing images thereof. It will be appreciated that this shaft speed and position data 32 or other relevant data, may be acquired and delivered to the local monitoring computer 8 by any known or suitable apparatus and method (e.g., without limitation, optical sensor signal; shaft phasor signal; timing of the images being captured).

Once the shaft data 32 is received by the exemplary local monitoring computer 8, the local monitoring computer 8 transmits imager control signals 34 to trigger the CCD camera 4 to capture blade images. Blade image data 36 is then transmitted back to the computer 8 and analyzed for blade defects. The complete method of visual inspection of the present invention and the analysis of the capture images is discussed in greater detail hereinafter.

The exemplary optical inspection system 2 further includes a local storage bank 9 for storing selected blade images. Digitized images such as those taken by the exemplary CCD camera 4 frequently require large amounts of computer storage space. Therefore, it is often desirable to detect blade defects on-site and forward only selected images to other information processing systems (not shown). The local storage bank 9 provides sufficient memory to store selected images. This enables the images to be subsequently retrieved, for example, for comparison with newly acquired images or for fusing with other stored images to better detect blade defects. For example, other sensors (not shown) may gather additional turbine data (e.g., without limitation, temperature; vibration; emission spectrogram) which are acquired, controlled by and monitored by the control and monitoring systems 30 may be fused with the images obtained during turning gear operation. As employed herein, "fused" refers to the combination of different sensor 29 data, which may also be referred to as sensor fusion or information fusion. Specifically, the present invention contemplates combining or "fusing" different types of data from a number of different sensors 29 in any suitable combination or manner, for purposes of analysis, as opposed to viewing or analyzing one sensor's data individually. Sensor fusion is employed, for example, to increase sensitivity and selectivity of blade defect detection algorithms and software programs. For instance, while images and other sensor data may be relatively inconclusive individually, as to whether a blade has a defect, when a variety of data is combined or fused, it is likely to more conclusively indicate whether or not a blade defect is or is not present.

As shown in FIG. 1, data, such as alarm signals 38, reference image data 40 and control and status signals 42 can be transmitted between the local monitoring computer 8 and the other monitoring and control systems 30 for facilitating the reliable and efficient detection of blade defects and preventing the turbine 50 from being returned to service with a defective turbine blade 52. The manner in which the blade images are analyzed may be by way of any known or suitable method, expressly including, without limitation, automated methods and manual visual inspections. One such known imaging method is the Automated Thermal Nondestructive Testing (NDT) technology deployed by Computerized Thermal Imaging (CTI), Inc. of 1719 W. 2800 S. Ogden, Utah 84401 for applications ranging from analysis of an engine's turbine blade defects to medical and industrial applications. Additional information about CTI's imaging technology can be found at the Internet website address: <http://www.cti-net.com>.

Figure 2:
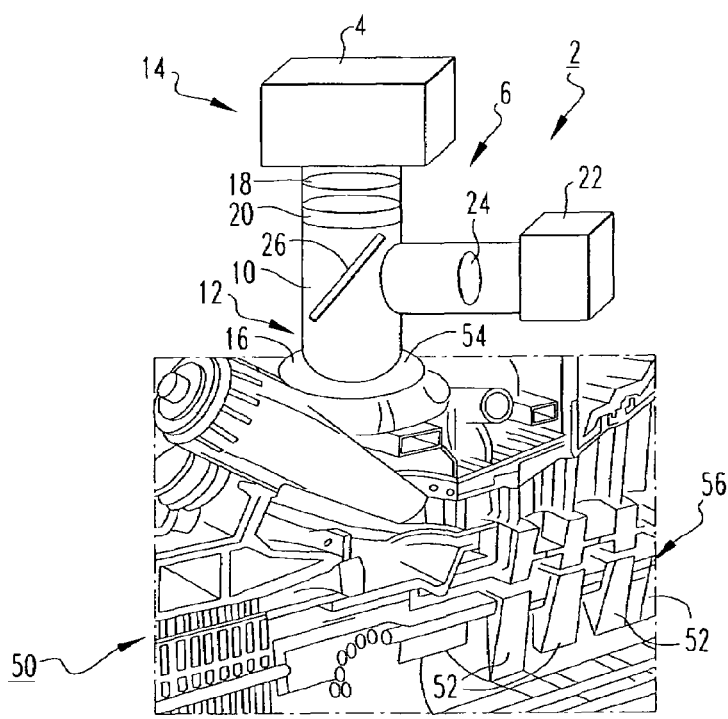
FIG. 2 is a schematic representation of the imager viewing device and illuminating assembly of the optical inspection system of FIG. 1 as employed at an inspection port of the turbine, with a portion of the turbine cut away to show internal structures.

FIG. 2 shows the camera 4 and illuminating assembly 6 of the exemplary optical inspection system 2 as employed to visually inspect the exemplary combustion turbine 50 at turning gear. The exemplary optical passage 10 and camera 4 combination employs the Scheimpflug principle to focus on the maximum accessible area of the blade 50. The Scheimpflug principle is a well known geometric principle in the imaging art, which affects correct focus of the camera 4. It will, of course, be appreciated that any known or suitable means other than the exemplary Scheimpflug principle could alternatively be employed to focus on the maximum accessible blade area 50. For example, alternatively, a less advantageous way to keep the blade 52 in focus would be to increase the depth of field by varying imager 4 and viewing device 10 parameters such as by reducing the lens opening or focal length or increasing the distance from the camera 4 to the blade 52. However, such measures have a penalty in image brightness, thereby requiring a longer exposure or integration time and consequent image blur.

As shown, the optical passage 10 has a first end 12 and a second end 14. In a preferred embodiment, the CCD camera 4 is coupled to the first end 12 of the passage 10. The second end 14 includes a window 16. The window can be structured to fit into an existing inspection port 54 or alternatively can be designed to fit into the second end 14 of the optical passage 10 or as part of the turbine 50. The exemplary window 16 is made from a temperature-resistant material, such as, for example, without limitation, fluorite, which permits unobstructed viewing of the turbine blades 52 during the turning gear operation while functioning as a thermal barrier protecting the camera 4 and electrical components of the inspection system 2 from internal heat, pressure and chemistry of the turbine 50. It will be appreciated that the window 16 may be positioned in such a configuration as to allow viewing of the blades 52 axially, radially or at some intermediate angle. It will also be appreciated that any suitable alternative protective mechanism, such as a value (not shown) or mechanical latch (not shown) could be employed to temporarily open a viewing passage into the turbine 50, rather than the exemplary temperature-resistance window 16, in order to isolate the equipment when the turbine 50 is running.

The exemplary optical passage 10 further includes an optional high-speed shutter 18. The high-speed shutter 18 may comprise, for example, an optical interrupter or a magneto-optic switch (not shown), which are well known devices in the image-capturing art, that can compensate for longer integration times required by some cameras. As shown, the exemplary high-speed shutter 18 is located adjacent the camera 4 proximate the second end 14 of the optical passage 10. The exemplary optical passage 10 also includes an image intensifier 20 for use in cases where additional blade illumination is necessary. The exemplary image intensifier is shown generically as reference 20 located within the optical passage 10 beneath high-speed shutter 18. It will be appreciated that the components (e.g, without limitation, window 16, shutter 18, image intensifier 20) of the exemplary optical inspection system 2 and optical passage 10 thereof could alternatively be configured in any suitable arrangement other than that illustrated and described.

Continuing to refer to FIG. 2, as previously discussed, the optical inspection system 2 of the present invention also includes an illuminating assembly 6. The illumination assembly 6 provides the necessary light source required to sufficiently illuminate the turbine blades 52 for quality image capturing thereof. The illumination assembly 6 includes an illuminating device 22 which may comprise a continuous light source, an episcopic illuminator or a flash, such as a Xenon flash, or any other known or suitable illuminating device. For example, without limitation, alternative methods and apparatus (not shown) for providing illumination of the dark interior of the turbine 50 include incorporation of the fiber optic light pipes (not shown) into the camera 4 optical assembly in order to conduct light from outside the turbine 50; allowing sufficient surplus area in the temperature-resistant window 16 to permit use of an outside illuminator (not shown) or flash (not shown); illuminating the blades 52 through a second optical window (not shown); and using blackbody radiation of internal turbine 50 components in the early portion of the turning gear operation. It will be appreciated that these and other illumination methods and apparatus and combinations thereof may be employed independently or with the exemplary optical inspection system 2 in order to improve quality (i.e., contrast; sharpness) of the blade images.

As shown, the exemplary illuminating assembly 6 is coupled to the intermediate portion of the optical passage 10 and includes a lens or lens system (shown generically as reference 24 in FIG. 2). The lens or lens system 24, when placed in front of the flash or continuous light source 22 functions to redirect light emitted, thereby concentrating the light (i.e., forming a beam) and optimizing the amount of light entering into the optical passage 10 and illuminating the blades 52. Upon entering the optical passage 10, the concentrated light is then deflected by a reflective member, such as the exemplary half-silvered mirror 26. The reflective member 26 can be moved (i.e., rotated) within the optical passage 10 in order to direct the light in a manner which best illuminates the turbine blades 52. Adjustment of the exemplary half-silvered mirror 26 is one of the viewing device 10 functions which may be controlled by the local monitoring computer 8, as previously discussed. Alternatively, it will be appreciated that such functions may be manually controlled.

Figure 3:
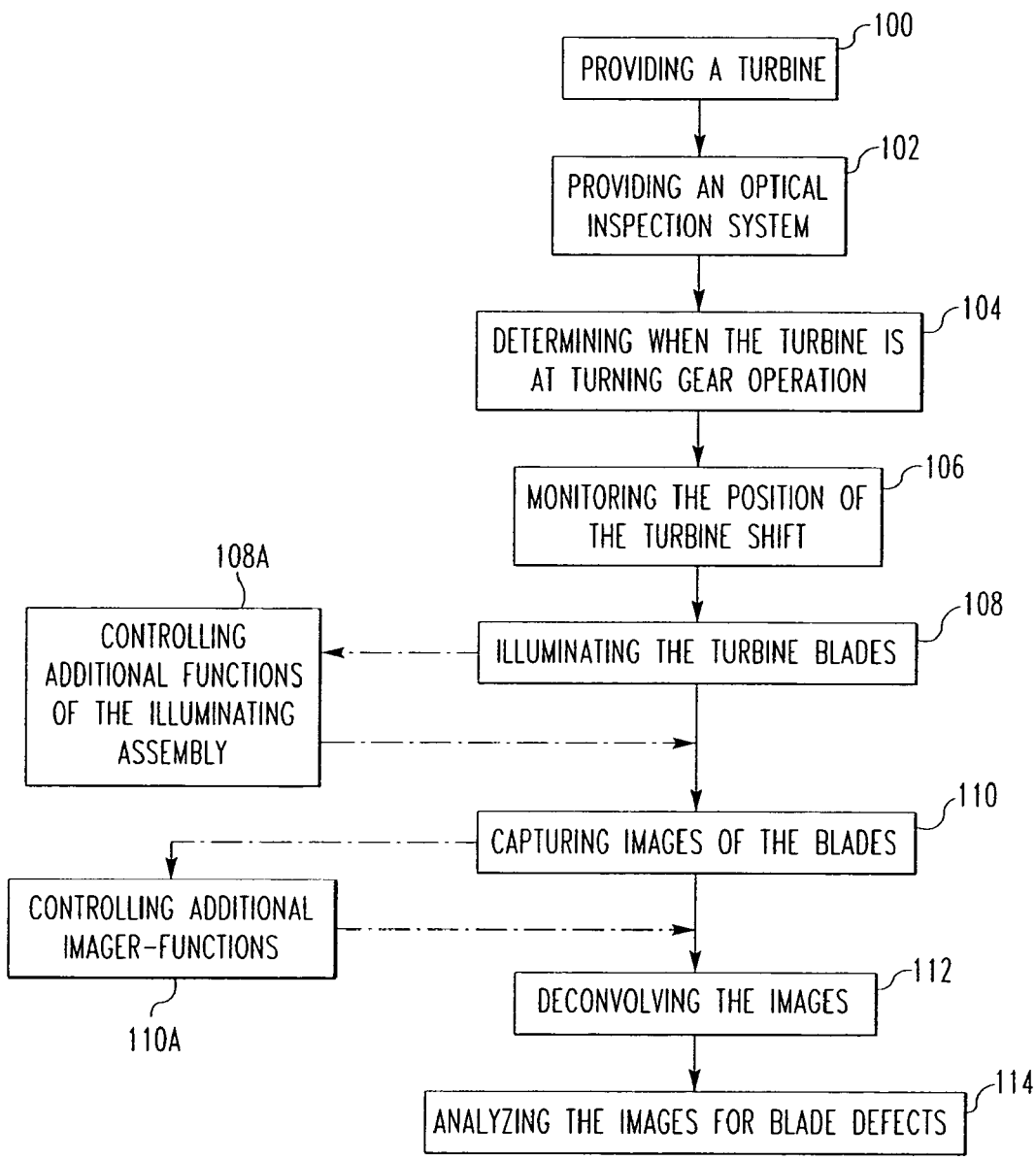
FIG. 3 is a flow diagram of the steps performed in accordance with a method of visually inspecting the blades of a turbine at turning gear operation, in accordance with an embodiment of the invention.

FIG. 3, shows the steps for visually inspecting the blades 52 of the turbine 50 at turning gear in accordance with the exemplary method of the present invention. Steps 100 and 102 are to provide the turbine 50 and optical inspection system 2, respectively. Step 104 is to determine when the turbine 50 is on the turning gear operation. This step 104, as previously discussed, may be accomplished using sensor data 32 acquired from sensors 29 disposed at the turbine 50. Alternatively, this determination could be made based upon information gathered from other monitoring apparatus and control systems (shown generically in schematic form as reference 30 in FIG. 2). Step 106 involves monitoring the shaft 56 position of the turbine 50 during the turning gear operation in order to determine when each blade 52 is in view of the inspection port 54 and the camera 4 coupled thereto. Step 106 is accomplished using, for example, the shaft phasor signal in order to synchronize the camera 4 to blade 52. This timing signal in conjunction with, for example, a programmable trigger circuit, may be used to trigger the camera 4 when the desired blade 52 is in the camera's field of view. The next step 108 is to illuminate or provide the necessary light for effective imaging of the blades 52. Once illuminated, blade images are captured 110, deconvolved 112 and analyzed for defects 114. Deconvolution is a process which is well known in the image development art wherein the image is cleaned or the clarity of the image improved, often by a known computer software program, in order to reduce, for example, blur or distortion.

By way of example, without limitation, known deconvolution algorithms include the Rapid Image Deconvolution (RIDE) algorithms utilized by Soft Imaging System Corporation's analySIS analytical software. Soft Imaging System Corporation has North American Headquarters in Lakewood, Colo. at 12596 West Bayaud Avenue, Suite 300, Lakewood, Colo. 80228. Additional information about the company's analySIS imaging software can be found at the Internet website: <http"//www.soft-imaging.net>. Briefly, the analySIS software increases the sharpness of high resolution pictures using one of three RIDE algorithms: "nearest Neighbor," "no neighbor" or "inverse filter." See, e.g., *Image Deconvolution: Soft Imaging System*, Photonics Spectra, Innovative Products October 2002 Ed. at <http:/photonics.com/spectra/newprods/XQ/ASP/newprodidi.5308/QX/read.htm>, which is hereby incorporated herein by reference.

As previously discussed, these steps may be automated by the exemplary local monitoring computer 8 (FIG. 1). Additionally, step 108 of illuminating the blades and step 110 of capturing blade images may optionally further include steps 108A and 110A of controlling various functions of the illuminating assembly 6 (i.e., deflector 26 angle; lens 24 speed; flash speed) and the imager 4 (i.e., integration speed; high-speed shutter 18; image intensifier 20), respectively. These steps may also be automated by the exemplary computer 8.

In practice, it will often not be necessary to capture images of each blade 52 every time it passes the inspection port 54 and imager 4 coupled thereto. The frequency with which images are captured may be established and set by way of timing of the imager or may be controlled from data (e.g., 38, 40, 42) (FIG. 1) of other monitoring and control systems 30 (FIG. 1), as previously discussed. For example, the time of exposure can be determined by the flash 22 duration and, if a continuous light source is used, the exposure time is controlled by the camera shutter 18. One of the key advantages of the present invention is the fact that there are no requirements for shutter speed because the blade 52 rotational velocity is relatively slow (i.e., 3-5 RPM) during turning gear operation. Specifically, the exemplary CCD camera 4 has a typical integration or exposure time of 1 millisecond. Thus the turbine blade 52 would move only slightly (i.e., about 0.020 inches) during exposure. The exemplary Xenon flash provides a 50-microsecond exposure, in which time only nominal (i.e., about 0.0004 inches) blade 52 movement occurs. Accordingly, this combination will provide excellent image resolution to inspect the thermal barrier coating (TBC) of the blades 52. Therefore, the present invention provides an economical method and apparatus for capturing and reliably analyzing blade images with minimal turbine 50 downtime.

Figure 4:
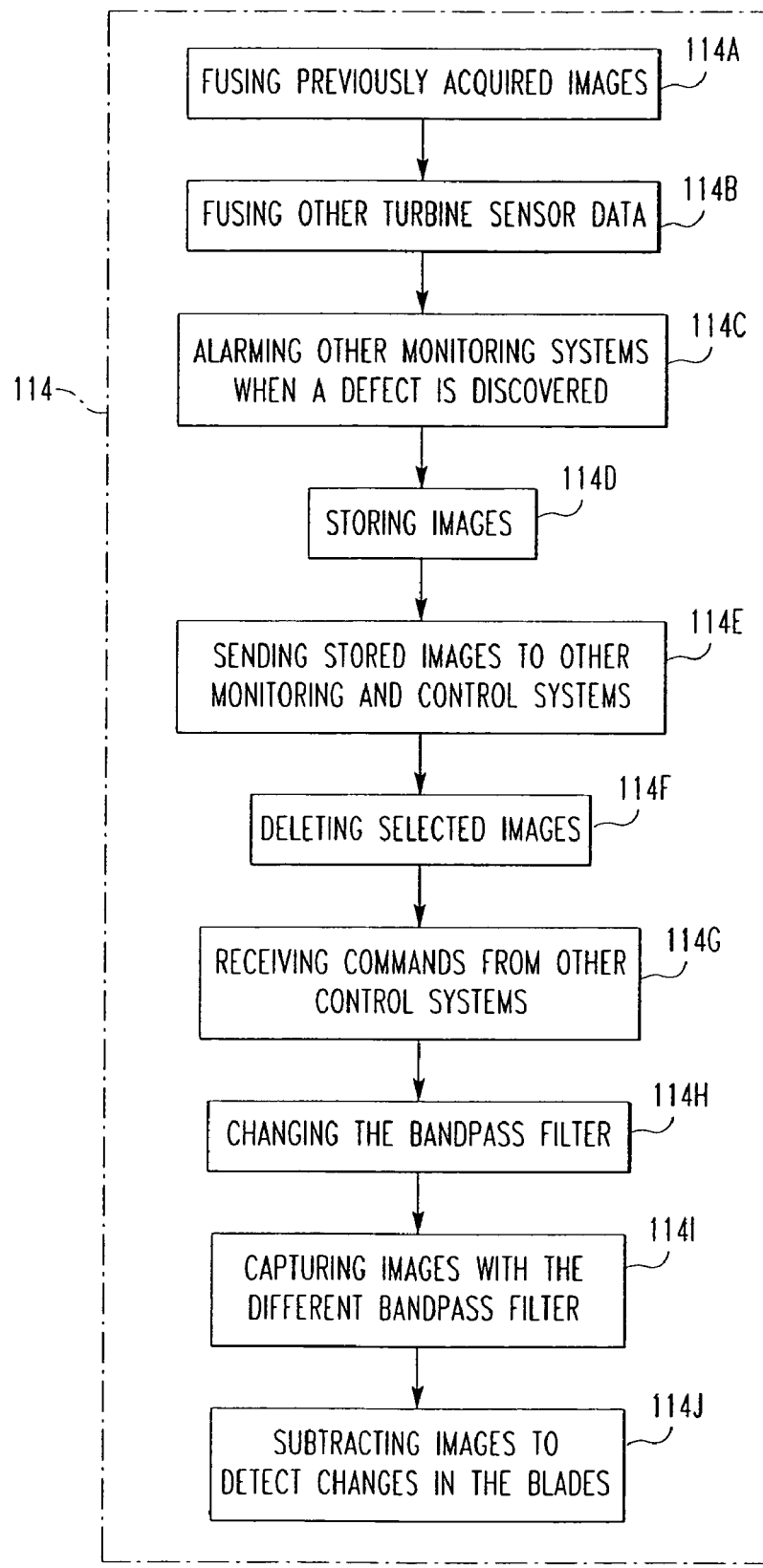
FIG. 4 is a flow diagram of optional additional step of analyzing the images for blade defects further to the method of FIG. 3.

FIG. 4 shows optional additional steps which may be employed, individually or in any suitable combination, further to step 114 of analyzing the images, in order to determine if any of the blades 52 have a defect which might endanger the turbine 50. The exemplary optional analysis steps include: step 114A, fusing previously acquired images of a particular blade 52 with the most recent images of the same blade 52; step 114B, fusing other turbine sensor data and output of other monitoring systems 30 (FIG. 1); step 114C alerting (i.e., electronic alarm signal; visible alarm; audible alarm) other monitoring and control systems 30 (FIG. 1) when an unsafe blade defect is detected; step 114D storing selected captured images in the local storage bank 9; step 114E, sending stored images to the other monitoring and control systems 30 (FIG. 1) upon command; step 114F, deleting selected images from the local storage bank 9 when they are no longer useful (i.e., after expiration of an established expiry date); step 114G, receiving other commands from other monitoring and control systems 30 (FIG. 1); step 114H, substituting different bandpass filters (not shown); step 114I capturing images with the different bandpass filter in order to inspect for different defects (i.e., cracks and other blade degradation, generally); and step 114J, subtracting images taken at different times or with different filters in order to detect changes in blade defects. The specific details of each of the foregoing optional steps were previously discussed herein with respect to FIGS. 1 and 2 and the corresponding disclosure of the exemplary optical inspection system 2 and operation thereof.

Accordingly, the method of visually inspecting turbine blades 52 while the turbine 50 is at turning gear and the optical inspection system 2 of the present invention provide a cost efficient, reliable way of detecting blade defects while minimizing the amount of turbine downtime and disadvantages associated therewith.

It will be appreciated that although method of visual inspection of the present invention has been described herein as a computer automated procedure wherein, for example, blade images are captured, processed and analyzed by the exemplary local monitoring computer 8, obviously the captured images could also be manually, visually inspected and analyzed for blade 52 defects. It will also be appreciated that the method of inspection of the present invention can be applied, for example, after the turbine has been shut down but while it is still rotating from inertia or while the turbine is, for example, being rotated by hand or driven by an external motor (not shown) or any other suitable apparatus, and also at times other than during the turning gear operation.

While specific embodiments of the invention have been described in detail, it will be appreciated by those skilled in the art that various modifications and alternatives to those details could be developed in light of the overall teachings of the disclosure. For example, the imager 4, illuminating assembly 6 and viewing device 10 do not have to be coupled together as shown in the figures and discussed herein. Alternatively, for example, without limitation, the imager 4 and illuminating assembly 6 could be one integrated device (not shown) which is directly attached to the turbine inspection port 54 (not shown). Additionally, although the exemplary optical passage 10 is shown as a tube, it will be appreciated that any known or suitable optical passage shape and configuration could alternatively be employed. Accordingly, the particular arrangements disclosed are meant to be illustrative only and not limiting as to the scope of the invention which is to be given the full breadth of the claims appended and any and all equivalents thereof.

What is claimed is:

1. An optical inspection system for visually inspecting a blade of a turbine, said turbine including an inspection port said optical inspection system comprising:

an imager arranged to capture images of said blade while said turbine is at a turning gear operation;
a viewing device coupled to said imager and structured to permit said imager to view said blade through the inspection port of said turbine; and
an illuminating assembly arranged to illuminate said blade while said imager captures images thereof,
wherein said viewing device includes a temperature-resistant window.

2. The optical inspection system of claim 1 further including a local monitoring computer; wherein said imager is a computer-controlled camera; and wherein said local monitoring computer is adapted to control said camera in order to automate the capturing of images of said blade and the inspection of said images for blade defects.

3. An optical inspection system for visually inspecting a blade of a turbine, said turbine including an inspection port, said optical inspection system comprising:

an imager arranged to capture images of said blade while said turbine is at a turning gear operation;
a viewing device coupled to said imager and structured to permit said imager to view said blade though the inspection port of said turbine; and
an illuminating assembly arranged to illuminate said blade while said imager captures images thereof;
wherein said viewing device is an optical passage structured to maximize the amount of said blade which can be viewed through said inspection port, said optical passage including a first end, a second end and an intermediate portion therebetween; wherein the first end of said optical passage is coupled to said inspection port; and wherein said imager is coupled to the second end of said optical passage.

4. The optical inspection system of claim 3 wherein said optical passage further includes a high-speed shutter disposed proximate the second end thereof, adjacent said imager.

5. The optical inspection system of claim 3 further includes an image intensifier.

6. The optical inspection system of claim 3 wherein said illuminating assembly includes an illuminating device, a lens for concentrating light emitted from said illuminating device, and a deflector for directing the concentrated light onto said blade; and wherein said illuminating assembly is coupled to the intermediate portion of said optical passage.

7. The optical inspection system of claim 6 wherein said illuminating device is selected from the group consisting of a flash and a continuous light source.

8. The optical inspection system of claim 6 wherein said deflector is a half-silvered mirror; and wherein said half-silvered mirror is adjustable in order to deflect light emitted from said illuminating device onto said blade.

9. A method of visually inspecting a turbine during a turning gear operation comprising the steps of:

providing a turbine including a plurality of blades and an inspection port for viewing said plurality of blades, said blades being coupled to a rotating shaft;
providing an optical inspection system for visually inspecting at least one of said plurality blades through said inspection port, said optical inspection system including an imager, a viewing device coupled to said imager and adapted to capture images of said at least one of said plurality of said blades through said inspection port, and an illuminating assembly adapted to illuminate said at least one of said plurality of blades while said imager captures images thereof;
determining when said turbine is in said turning gear operation;

monitoring the position of the shaft of said turbine in order to determine when said at least one of said plurality of blades is in proper view for capturing images;

illuminating said at least one of said plurality of blades;

capturing images of said at least one of said plurality of blades;

deconvolving the images; and analyzing the images in order to determine whether or not any of said plurality of blades has a defect.

10. The method of claim 9 wherein said optical inspection system includes a local monitoring computer; and wherein said local monitoring computer automates one or more of the steps of said method of visually inspecting a turbine during a turning gear operation.

11. The method of claim 10 wherein said step of analyzing the images for blade defects includes fusing previously acquired images of a blade with the most recently acquired image of the same blade.

12. The method of claim 10 wherein said step of analyzing the images for blade defects includes fusing turbine sensor data and turbine monitoring system output.

13. The method of claim 10 wherein said step of analyzing the images for blade defects includes alarming other monitoring systems when a defect is detected.

14. The method of claim 10 wherein said step of analyzing the images for blade defects includes selecting certain captured images for storage in a local storage bank.

15. The method of claim 14 including sending selected stored images to other monitoring and control systems.

16. The method of claim 14 including deleting selected images from said local storage bank when the images are no longer useful.

17. The method of claim 10 wherein said imager includes a bandpass filter; and wherein said step of analyzing the images for blade defects includes the steps of changing the bandpass filter and capturing images with the different bandpass filter.

18. The method of claim 10 wherein said step of analyzing the images for blade defects includes subtracting images taken at different times or with different bandpass filters in order to detect changes in said blades.

19. The method of claim 10 wherein said step of illuminating the blades further includes the step of controlling functions of the illuminating assembly.

20. The method of claim 10 wherein said step of capturing the images further includes the step of controlling functions of the imager.

* * * * *